United States Patent [19]

Yeater et al.

[11] Patent Number: 5,231,217
[45] Date of Patent: Jul. 27, 1993

[54] PROCESS FOR THE PREPARATION OF AMINE-TERMINATED COMPOUNDS

[75] Inventors: Robert P. Yeater, Moundsville, W. Va.; Robson Mafoti; Josef Sanders, both of Pittsburgh, Pa.

[73] Assignee: Miles Inc., Pittsburgh, Pa.

[21] Appl. No.: 672,264

[22] Filed: Mar. 20, 1991

[51] Int. Cl.$^5$ .......................................... C07C 209/00
[52] U.S. Cl. ...................................... 560/44; 560/169; 558/265; 558/269; 564/135; 564/337; 564/346; 564/393; 564/396; 564/397; 564/468; 564/471; 564/472; 528/271; 528/332
[58] Field of Search ............... 564/393, 134, 135, 199, 564/337, 346, 393, 396, 468, 471, 472; 528/332, 271; 560/44, 169; 558/265, 269

[56] References Cited

U.S. PATENT DOCUMENTS

| | | | |
|---|---|---|---|
| 3,669,729 | 6/1972 | Seiner | 117/161 UA |
| 3,691,112 | 9/1972 | Grogler et al. | 260/2.5 AM |
| 3,778,474 | 12/1973 | Stocker | 564/199 |
| 4,359,584 | 11/1982 | Merger et al. | 564/398 |

FOREIGN PATENT DOCUMENTS 1598720  8/1970  France ................................. 564/393
0179140  3/1989  Japan.

OTHER PUBLICATIONS

Zabicky, The Chemistry of Amides, 1970, Interscience Publishers, 96-97.

Primary Examiner—Allen J. Robinson
Assistant Examiner—Shailendra Kumar
Attorney, Agent, or Firm—Joseph C. Gil; Godfried R. Akorli

[57] ABSTRACT

The present invention is directed to a novel solvent-free process for preparing amine terminated compounds by reacting a polyfunctional acetoacetic acid ester with either ammonia or an organic compound which contains one or more primary amino groups in the presence of an acidic catalyst selected from the group consisting of (i) boron trifluoride etherate and (ii) organic acids having pKa values of from 0.1 to 0.8.

8 Claims, No Drawings

PROCESS FOR THE PREPARATION OF AMINE-TERMINATED COMPOUNDS

BACKGROUND OF THE INVENTION

1. Field of the Invention

The present invention relates to a process for preparing amine-terminated compounds. More specifically the present invention relates to a solvent-free process for preparing amine terminated compounds by reacting polyfunctional acetoacetic acid esters with ammonia or primary amine containing compounds.

2. Brief Description of the Prior Art

The art known processes for the preparation of amine-terminated compounds by reacting polyfunctional acetoacetic acid esters with ammonia or amines, invariably, involves the use of solvents. U.S. Pat. No. 3,691,112 (and the corresponding German Offenlegungsschrift 1,935,484) describes the preparation of compounds by reacting a polyfunctional acetoacetic acid ester with ammonia or an aliphatic or aromatic primary or secondary monoamine. The reaction is conducted in the presence of a solvent (hydrocarbons, such as benzene and toluene, and halogenated hydrocarbons, such as chloroform and carbon tetrachloride, are disclosed) and a catalyst. Suitable catalysts are described as "acids, for example hydrochloric acid, formic acid or glacial acetic acid, or other compounds such as iodine, cation exchangers or active alumina."

U.S. Pat. No. 3,666,726 (and the corresponding German Offenlegungsschrift 1,935,485) describes the preparation of similar compounds by reacting a polyfunctional acetoacetic acid esters with aliphatic aminoalcohols or diamines of different reactivity towards acetoacetic acid esters, e.g., those which contain primary and secondary or, alternatively, aliphatic and aromatic amino groups in the molecule. All of the diamines disclosed contain at least one aliphatic amino group. The reaction is conducted in the presence of a solvent (hydrocarbons, such as benzene and toluene, and halogenated hydrocarbons, such as chloroform and carbon tetrachloride, are disclosed) and a catalyst. Suitable catalysts are described as "acids, for example hydrochloric acid, formic acid or glacial acetic acid, or other compounds such as iodine, cation exchangers or active alumina." The reference does not describe the use of any specific polyamines where the amino groups are all directly attached to aromatic groups.

Commonly assigned U.S. application Ser. No. 07/562,293 discloses a process for preparing amine terminated compounds by reacting a polyfunctional acetoacetic acid ester with either ammonia or an organic compound which contains one or more primary amino groups in the presence of a solvent and an acidic catalyst selected from the group consisting of (i) boron trifluoride etherate and (ii) organic acids having pKa values of from 0.1 to 0.8.

By this invention, there is provided a solvent free process for preparing amine terminated compounds.

SUMMARY OF THE INVENTION

In accordance with the foregoing, the present invention encompasses a solvent-free process for preparing an amine terminate compound comprising reacting a polyfunctional acetoacetic acid ester with either ammonia or an organic compound which contains one or more primary amino groups in the presence of an acidic catalyst selected from the group consisting of (i) boron trifluoride etherate and (ii) an organic acid having pKa values of from 0.1 to 0.8; said process is characterized in that the reaction occurs in the absence of a solvent. The preferred organic acid is trifloro acetic acid.

By the term "polyfunctional acetoacetic acid ester" is meant that the acetoacetic acid ester contains two or more acetoacetate groups.

Specifically, in preparing the amine terminated compound without using a solvent, one can lower the cost of manufacturing, and in some instances avoid problems associated with the use of solvents. The resultant amine-terminated compounds showed no significant differences in physical properties. This and other aspects of the invention are more fully described hereinbelow.

DETAILED DESCRIPTION OF THE INVENTION

As would be realized, the reaction of acetoacetates with amines is an equilibrium reaction, wherein reaction water is removed by azeotropic distillation using a suitable solvent like chloroform or toluene. Considering the importance of the solvent in the reaction, it was quite surprising that the process of this invention could be conducted successfully in the absence of a solvent.

Accordingly, the present invention is directed to a novel solvent-free process for preparing amino group containing compounds. More particularly, the present invention is directed to a novel solvent-free process for the preparation of an amine-terminated compound by reacting a polyfunctional acetoacetic acid ester with either ammonia or an organic compound which contains one or more primary amino groups in the absence of a solvent and an acidic catalyst selected from the group consisting of (i) boron trifluoride etherate and (ii) organic acids having pKa values of from 0.1 to 0.8. By this invention, it is possible to produce a wide variety of different amines having a wide variety of different reactivities by selection of the primary amino compound used in the preparation thereof.

In the preferred process, primary diamines are reacted with the polyfunctional acetoacetic acid esters. The amines produced herein are useful in the production of isocyanate addition products, such as, e.g., by reaction with organic isocyanates.

The polyfunctional acetoacetic acid esters useful herein are produced by techniques generally known in the art. For example, the acetoacetic acid esters may be produced according to the processes described in U.S. Pat. Nos. 3,666,726 and 3,691,112, the disclosures of which are herein incorporated by reference. In general, the acetoacetic acid esters can be produced by reacting polyols with diketenes, or by transesterifying alkyl acetoacetates with polyols. The transesterification technique is the presently preferred technique. In general, the transesterification reaction is conducted at temperatures ranging from 100° to 210° C., preferably from 160° to 210° C. for periods of time ranging from 2 to 8 hours. If desired, transesterification catalysts, such as dibutyltin oxide and tetrabutyl titanate, can be used.

The polyols useful in producing the polyfunctional acetoacetic acid esters are of the type generally used in polyurethane chemistry. The polyols useful herein typically have molecular weights of from 62 to 12,000 and preferably 192 to 8000, and hydroxyl functionalities of from 2 to 6 and preferably 2 to 4. Examples of suitable polyols include the polyesters, polyethers, polythioethers, polyacetals, polybutadienes and polycarbonates containing 2 to 6 hydroxyl groups of the type known for the production of polyurethanes. The polyethers suitable for use in accordance with the invention are known and may be obtained, for example, by polymerizing epoxides such as ethylene oxide, propylene oxide, butylene oxide, tetrahydrofuran, styrene oxide or epichlorohydrin in the presence of $BF_3$ or by chemically adding these epoxides, preferably ethylene oxide and propylene oxide, in admixture or successively to components containing reactive hydrogen atoms such as water, alcohols or amines. Examples of alcohols and amines include low molecular weight diols, triols and tetrols, 4,4'-dihydroxy diphenyl propane, sorbitol, aniline, ammonia, ethanolamine and ethylene diamine.

Suitable examples of polyesters include the reaction products of polyhydric, preferably dihydric alcohols (optionally in the presence of trihydric alcohols), with polyvalent, preferably divalent, carboxylic acids. Instead of using the free carboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic, and/or heterocyclic and may be unsaturated or substituted, for example, by halogen atoms. The polycarboxylic acids and polyols used to prepare the polyesters are known and described for example in U.S. Pat. Nos. 4,098,731 and 3,726,952, herein incorporated by reference in their entirety.

Suitable polythioethers, polyacetals, polycarbonates and other polyhydroxyl compounds are also disclosed in the above-identified U.S. patents. Finally, representatives of the many and varied polyols which may be used in accordance with the invention may be found for example in High Polymers, Volume XVI, "Polyurethanes, Chemistry and Technology," by Saunders Frisch, Interscience Publishers, New York, London, Vol. I, 1962, pages 32–42 and 44–54, and Volume II, 1964, pages 5–6 and 198–199; and in Kunststoff-Handbuch, Vol. VII, Vieweg-Hochtlen, Carl Hanser Verlag, Munich, 1966, pages 45–71.

Polyols useful herein also include materials which are typically used as chain extenders in polyurethane chemistry. Examples of such materials include ethylene glycol, 1,2- and 1,3-propane diol, 1,3- and 1,4- and 2,3-butane diol, 1,6-hexane diol, 1,10-decane diol, diethylene glycol, triethylene glycol, tetraethylene glycol, dipropylene glycol, tripropylene glycol, glycerol, trimethylol propane, and pentaerythritol.

The polyfunctional acetoacetic acid esters are preferably prepared by transesterifying any on the above noted polyols with lower alkyl acetoacetates. By "lower alkyl" is meant alkyl groups containing from one to five carbon atoms. Specific useful acetoacetates include methyl acetoacetate, ethyl acetoacetate, t-butyl acetoacetate, propyl acetoacetate and the like, with t-butyl acetoacetate being the presently preferred material. In preparing the acetoacetic acid esters herein, transesterification catalysts may be necessary. In preparing the polyfunctional acetoacetic acid esters, it is generally preferred that the reactants by used in amount such that one OH group is present for each acetoacetate group. However, it is also possible to use excess amounts of either reactant. In fact, in some cases it is preferred to use an excess of the acetoacetate to ensure complete reaction.

The polyfunctional acetoacetic acid ester is then reacted with either ammonia or a compound containing one or more primary amino groups, in the presence of a specified acidic catalyst.

Critical to the present invention in the case of aromatic amines, is the selection of the catalyst. The catalyst is selected from the group consisting of boron trifluoride etherate, and organic acids having pKa values of from 0.01 to 0.8. It has been found that use of catalysts having pKa values outside the noted range leads to side reactions which lead to solid products. In addition, only the noted catalysts lead to commercially acceptable yields. Of the acids tested, only trifluoroacetic acid (pKa: 0.23) and p-toluene sulfonic acid (pKa: 0.7) were found useful in preparing amines from aromatic amine compounds. Illustrative but non-limiting examples of other organic acids can be halogenated organic acids having pKa values of 0.1 to 0.8. The amount of catalyst is generally selected so as to be sufficient to allow reasonable reaction times. In practice, the catalyst is added in amounts of from 0.05 to 2.0 mol %, and preferably from 0.3 to 1.0 mol %, based on the equivalents of acetoacetate present. This corresponds to from 0.01 to 0.2% by weight, and preferably from 0.05 to 0.1% by weight based on the weight of the polyfunctional acetoacetic acid ester.

Useful amines which are to be reacted with the polyfunctional acetoacetic acid esters are ammonia, and primary aliphatic and aromatic amines. The useful amines are selected from the group consisting of ethylene diamine, hexamethylene diamine, 2-methyl-1,5-diaminopentane, isophorone diamine, methylene biscyclohexylamine, methylene bis-methylcyclohexylamine, diethylene triamine; triethylene tetramine; diethyltoluene diamine and the various isomers and isomer mixtures thereof; toluene diamine and the various isomers and isomer mixtures thereof; methylenebis(phenyl amine) and the various isomers and isomer mixtures thereof; 1,5-naphthalene diamine ; isophorone diamine; aniline; alkyl anilines; toluidine; t-butyl toluene diamine, and the various isomers and isomer mixtures thereof; di-t-butyl toluene diamine, and the various isomers and isomer mixtures thereof; methylenebis(o-dichloroaniline) ("MOCA"); 2,4-diaminoalkybenzenes, and homologues and isomers thereof having alkyl radicals of from 8 to 15 carbon atoms as described in published European Patent Application 58,368; and the like.

The amount of amine is generally selected so that one mole of amine is available for every acetoacetate equivalent. It is of course possible to react less than one mole amine with one equivalent of acetoacetate. This might result in a lower conversion if the reaction is terminated before all acetoacetate groups have reacted with amine groups, or in chain extension if all acetoacetate groups have reacted. On the other hand, in order to suppress chain extension and to obtain low viscosity products, it might be advantageous to use more than one mole amine per equivalent of acetoacetate. The unreacted amine can either be stripped off once the reaction is complete, or can remain in the product to serve as a chain extender, i.e., in a reaction with isocyanates.

The reaction is generally carried out at temperatures of from 40° to 200° C., preferably from 90° to 140° C., under excess pressure, reduced pressure, or, preferably, in the substantial absence of pressure. The process can be conducted continuously or discontinuously. In general, the acetoacetic acid ester, the amines, and the catalyst can be reacted in the following order: acetoacetylated polyol, followed by amine and the catalyst. The reaction is considered complete when, the IR spectrum, the peak at 1740 cm⁻ has disappeared and by the amount of water collected. The reaction time, of course, depends on the nature and the amounts of starting materials. In general, reaction times are between 1 and 6 hours. When the reaction is complete, the catalyst and any unreacted amine (if desired) are distilled off. The distillate can generally be recycled.

The invention is further illustrated but is not intended to be limited by the following examples in which all parts and percentages are by weight unless otherwise specified.

EXAMPLES

Example 1

In the first step, 700 pounds of 2000 MW poly(oxypropylene)diol and 125 pounds of tert-butyl acetoacetate were charged to a 100 gallon reactor equipped with mechanical agitation and a distillation column. The mixture, under a nitrogen pad, was heated to 160° C. with agitation over a period of 3.5 hours at which point distillation of tert-butanol began. The temperature was further raised in a two hour period to 200° C. and held for three hours. The temperature was lowered to 160° C. and the pressure reduced slowly to 5 mm Hg. The mixture was held at the reduced pressure for two hours to insure that removal of the tert-butanol was complete. This process yielded a pale yellow liquid with viscosity of 340 mPa.s at 25° C. and a carbonyl number of 50.

In the second step, 731.5 pounds of the acetoacetylated polyol above, 74.4 pounds 1,5-diamino-2-methylpentane, and 6.0 pounds diethyltoluenediamine (Baytek E-505, available from Bayer AG) were charged to a 100 gallon reactor equipped with mechanical agitation and a distillation column. To this well stirred mixture was added 0.28 pounds trifluoroacetic acid. The mixture was heated to 80° C. under a nitrogen pad. The pressure was then reduced to 5 mm Hg while concurrently raising the temperature to 110° C. The mixture was held at 110° C. and 5 mm Hg for 30 minutes to insure complete removal of the water. The process yielded a yellow liquid with amine number 91 and viscosity 2640 mPa.s @25° C.

Example 2

In the first step, 80 pounds of 6000 MW (poly(oxypropyleneoxyethylen)triol and 7.3 pounds of tert-butyl acetoacetate were charged to a 15 gallon reactor equipped with mechanical agitation and a distillation column. The mixture, under a nitrogen pad, was heated to 185° C. with agitation over a period of two hours at which point distillation of tert-butanol began. The temperature was further raised in a one hour period to 200° C. and held for three hours. The temperature was lowered to 160° C. and the pressure reduced slowly to 5 mm Hg. The mixture was held at the reduced pressure for two hours to insure that removal of the tert-butanol was complete. This process yielded a pale yellow liquid with viscosity of 1170 mPa.s at 25° C. and a carbonyl number of 30.

In the second step, 82.5 pounds of the acetoacetylated polyol above and 4.83 pounds toluene diamine (TDA) were charged to a 15 gallon reactor equipped with mechanical agitation and a distillation column. To this well stirred mixture was added 0.008 pounds trifluoroacetic acid. The mixture was heated to 90° C. under a nitrogen pad and held 30 minutes. The pressure was then reduced to 5 mm Hg over a one hour period and held for three hours. The process yielded a yellow liquid with amine number 49 and viscosity 6450 mPa.s @ 25° C.

Example 3

In the first step, 80 pounds of 1000 MW poly(oxypropylene)diol and 27.7 pounds of tert-butyl acetoacetate were charged to a 15 gallon reactor equipped with mechanical agitation and a distillation column. The mixture, under a nitrogen pad, was heated to 165° C. with agitation over a period of one hour at which point distillation of tert-butanol began. The temperature was further raised in a two hour period to 200° C. and held for two hours. The temperature was lowered to 160° C. and the pressure reduced slowly to 5 mm Hg. The mixture was held at the reduced pressure for three hours to insure that removal of the tert-butanol was complete. This process yielded a pale yellow liquid with a carbonyl number of 98.

In the second step, 70 pounds of the acetoacetylated polyol above and 21 pounds diethyl TDA (Baytek E-505) were charged to a 15 gallon reactor equipped with mechanical agitation and a distillation column. To this well stirred mixture was added 0.007 pounds trifluoroacetic acid. The mixture was heated to 90° C. under a nitrogen pad and held 30 minutes. The pressure was then reduced to 5 mm Hg over a one hour period and held three hours. The process yielded a yellow liquid with amine number 140 and viscosity 10,600 mPa.s @ 25° C.

Example 4

In the first step, neopentyladipate of MW 2000 (Formres 55, available from Witco) was acetoacetylated according to the first step in Example 2.

In the second step, 1500 g of the acetoacetylated neopentyladipate above and 246 g diethyltoluenediamine (Baytec A505, available from Bayer AG), was charged to a 3 liter three-neck flask equipped with mechanical stirrer and distillation apparatus. To this well mixed mixture was added 0.6 g trifluoroacetic acid. The mixture was heated to 80° C. under a nitrogen pad. The pressure was then reduced to 5 mm Hg while concurrently raising the temperature to 110° C. The mixture was held at 110° C. and 5 mm Hg for 30 minutes to insure complete removal of the water. The process yielded a brownish liquid with an amine number of 85 and a viscosity of 30,000 mPa.s @ 60° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A solvent-free process for the preparation of an aromatic amine-terminated compound comprising reacting a polyfunctional acetoacetic acid ester with either ammonia or an organic compound which contains one or more primary amino groups in the presence of an acidic catalyst selected from the group consisting of (i) boron trifluoride etherate, and (ii) organic acids having pKa values of from 0.1 to 0.8; said process is characterized in that the reaction occurs in the absence of a solvent.

2. The process of claim 1, wherein said organic acid is a halogenated organic carboxylic acid.

3. The process of claim 2, wherein said organic acid is a halogenated acetic acid.

4. The process of claim 3, wherein said halogenated acetic acid is trifluoroacetic acid.

5. The process of claim 1, wherein said polyfunctional acetoacetic acid ester is prepared by reacting a $C_1$ to $C_5$ alkyl acetoacetate with an organic compound containing from 2 to 6 hydroxyl groups and having a molecular weight of from 62 to about 12,000, in a ratio such that one mole of acetoacetate is used for each hydroxyl group.

6. The process of claim 5, wherein said polyfunctional acetoacetic acid ester is prepared by reacting a $C_1$ to $C_5$ alkyl acetoacetate with a organic compound containing from 2 to 4 hydroxyl groups and having a molecular weight of from 192 to 8,000, in a ratio such that one mole of acetoacetate is used for each hydroxyl group.

7. The process of claim 1, wherein said organic compound containing primary amino groups is an aromatic diamine.

8. The process of claim 7, wherein said aromatic diamine is selected from the group consisting of toluene diamines, alkyl-substituted toluene diamines, methylenebis(phenyl amines), alkyl-substituted methylenebis(phenyl amines), 1,5-napthalene diamine, and phenylene diamines.

* * * * *